(12) United States Patent
Wood et al.

(10) Patent No.: US 9,358,508 B2
(45) Date of Patent: Jun. 7, 2016

(54) DRYER AND WATER RECOVERY/PURIFICATION UNIT EMPLOYING GRAPHENE OXIDE OR PERFORATED GRAPHENE MONOLAYER MEMBRANES

(71) Applicant: LOCKHEED MARTIN CORPORATION, Bethesda, MD (US)

(72) Inventors: John A. Wood, Bethlehem, PA (US); Rebecca Schwartz, Chester Springs, PA (US); Paul J. Lilly, Brookeville, MD (US)

(73) Assignee: Lockheed Martin Corporation, Bethesda, MD (US)

( * ) Notice: Subject to any disclaimer, the term of this patent is extended or adjusted under 35 U.S.C. 154(b) by 114 days.

(21) Appl. No.: 14/261,234

(22) Filed: Apr. 24, 2014

(65) Prior Publication Data

US 2014/0318373 A1   Oct. 30, 2014

Related U.S. Application Data

(60) Provisional application No. 61/816,052, filed on Apr. 25, 2013.

(51) Int. Cl.
  *B01D 71/02* (2006.01)
  *B01D 53/22* (2006.01)
  (Continued)

(52) U.S. Cl.
  CPC ............ *B01D 71/021* (2013.01); *B01D 53/228* (2013.01); *B01D 53/268* (2013.01);
  (Continued)

(58) Field of Classification Search
  CPC .... B01D 53/228; B01D 53/268; B01D 63/06; B01D 71/021; B01D 71/024; B01D 71/06; B01D 2258/0266; B01D 2311/103; B01D 2313/23; C02F 1/447; C02F 11/12; C02F 2103/20; G01N 2030/146

USPC ..................... 95/52; 96/4, 11; 210/321.6, 240
  See application file for complete search history.

(56) References Cited

U.S. PATENT DOCUMENTS 3,367,850 A * 2/1968 Johnson ............. G01N 33/2847
  95/52
3,917,508 A * 11/1975 Greenfield ............... B01D 1/26
  159/13.2

(Continued)

FOREIGN PATENT DOCUMENTS

WO      2013010076 A1    1/2013

OTHER PUBLICATIONS

Chen et al. Self-Assembled Free Standing Graphite Oxide Membrane. Advanced Materials. vol. 21. pp. 3007-3011. 2009.

(Continued)

*Primary Examiner* — Jason M Greene
(74) *Attorney, Agent, or Firm* — Marsh Fischmann & Breyfogle LLP (57) ABSTRACT

Apparatuses and systems for removing water vapor from a gas stream and for providing water purification, recovery and/or concentration. The apparatuses and systems employ a graphene oxide or a perforated graphene monolayer membrane to separate liquid water molecules and/or water vapor molecules from gasses, liquids, and other substances such as a wet muck or an aqueous sample. In one embodiment, an apparatus for removing water from a gas or liquid stream includes a first lumen, a second lumen, and a graphene oxide membrane separating the first lumen from the second lumen. Water molecules within a humid gas or liquid stream introduced into the first lumen pass through the graphene oxide membrane into a dry gas stream introduced into the second lumen.

14 Claims, 4 Drawing Sheets

(51) Int. Cl.
*B01D 71/06* (2006.01)
*B01D 53/26* (2006.01)
*B01D 63/06* (2006.01)
*C02F 1/44* (2006.01)
*C02F 11/12* (2006.01)
*C02F 103/20* (2006.01)
*G01N 30/14* (2006.01)

(52) U.S. Cl.
CPC ............... *B01D 63/06* (2013.01); *B01D 71/06* (2013.01); *C02F 1/447* (2013.01); *B01D 71/024* (2013.01); *B01D 2258/0266* (2013.01); *B01D 2311/103* (2013.01); *B01D 2313/23* (2013.01); *C02F 11/12* (2013.01); *C02F 2103/20* (2013.01); *G01N 2030/146* (2013.01)

(56) References Cited

U.S. PATENT DOCUMENTS

| | | | | |
|---|---|---|---|---|
| 4,070,280 A | * | 1/1978 | Bray | B01D 61/08 210/321.67 |
| 4,316,774 A | | 2/1982 | Trusch | |
| 4,832,850 A | * | 5/1989 | Cais | B01D 61/08 210/638 |
| 4,879,041 A | * | 11/1989 | Kurokawa | B01D 61/364 210/640 |
| 5,034,025 A | | 7/1991 | Overmann, III | B01D 53/22 95/52 |
| 5,814,128 A | | 9/1998 | Jiang et al. | |
| 6,017,200 A | * | 1/2000 | Childs | B01D 61/06 417/390 |
| 6,059,857 A | * | 5/2000 | Ray | B01D 53/229 95/52 |
| 6,540,817 B1 | * | 4/2003 | Hachimaki | B01D 63/02 95/52 |
| 7,572,319 B2 | | 8/2009 | Tipler et al. | |
| 8,496,731 B2 | * | 7/2013 | Yukumoto | B01D 61/362 95/52 |
| 2002/0020298 A1 | * | 2/2002 | Drost | B01D 53/228 96/11 |
| 2005/0263456 A1 | | 12/2005 | Cooper et al. | |
| 2007/0044483 A1 | | 3/2007 | Refal-Ahmed et al. | |
| 2009/0101557 A1 | * | 4/2009 | Tsai | B01D 61/362 210/181 |
| 2009/0145847 A1 | * | 6/2009 | Spiegelman | B01D 53/22 210/321.6 |
| 2010/0176057 A1 | * | 7/2010 | Karnik | B01D 61/364 210/640 |
| 2011/0163296 A1 | | 7/2011 | Pace et al. | |
| 2012/0048804 A1 | * | 3/2012 | Stetson | B01D 61/02 210/321.6 |
| 2013/0199370 A1 | * | 8/2013 | Okada | B01D 53/228 95/52 |
| 2015/0122814 A1 | * | 5/2015 | Tichborne | B01D 53/268 96/4 |
| 2015/0153258 A1 | * | 6/2015 | Huemer | B01D 63/08 210/780 |
| 2015/0231577 A1 | * | 8/2015 | Nair | B01D 71/024 210/640 |

OTHER PUBLICATIONS

Nair et al. Unimpeded Permeation of Water Through Helium-Leak-Tight Graphene-Based Membranes. Science. www.sciencemag.org. vol. 335. pp. 442-444. Jan. 27, 2012.

* cited by examiner

DRYER AND WATER RECOVERY/PURIFICATION UNIT EMPLOYING GRAPHENE OXIDE OR PERFORATED GRAPHENE MONOLAYER MEMBRANES

RELATED APPLICATION INFORMATION

This application claims priority to U.S. Provisional Application Ser. No. 61/816,052, entitled "GRAPHENE OXIDE DRYER AND WATER RECOVERY/PURIFICATION UNIT" filed on Apr. 25, 2013, the entire contents of which are incorporated by reference herein as if set forth in full.

FIELD OF THE INVENTION

The present invention relates generally to the removal and recovery of water from gases, liquids and other substances.

BACKGROUND OF THE INVENTION

The chemical analysis of trace quantities of toxic substances by gas chromatograph/mass spectrometer (GC/MS) instruments requires the concentration of those substances on a trap, and subsequent release of those substances into an analytical column to separate the substances from each other on the way to the mass spectrometer. The analytical column may be negatively affected by water. In this regard, water vapor is a major problem for GC/MS systems, and must be eliminated as much as possible from the sample being injected for analysis. Trace analysis requires the concentration of substances of interest from about a liter of gas (usually air or helium, if the sample is purged from contaminated soil or water). Currently, commercial purge and trap systems used to concentrate samples for trace analysis by GC/MS incorporate 'water management' systems to remove water with the objective of minimally affecting the sample. However, those systems still do not function perfectly, and they add an additional several minutes to the analytical time for every sample while they cycle to remove the water.

The drying of samples prior to concentration for GC/MS systems has been done previously in two ways. The first was the use of Nafion®, a polar polymer. Nafion® tubing passes water and some other polar substances through it, while being impervious to most nonpolar substances. Nafion® is currently used as the membrane in hydrogen fuel cells, with minor use as a dryer. In prior years, perhaps up to about 20 years ago, air samples were put through Nafion® tubing to remove the water. It worked well for a lot of compounds, but fell short for polar compounds. In experiments conducted in the late 1970's, about 70% of methanol and 30% of ethanol went through the Nafion® with the water, and was lost. It was tested and used by the EPA in its Method TO-14 to dry sample air as it was being pumped into a sample container to greater than atmospheric pressure. It worked well for a number of toxic substances, but many of the polar toxic substances were lost through the Nafion® to such a degree that the method was eventually replaced. Therefore, as the government expanded its list of target substances, and those compounds included some very polar substances, a new solution was found.

Method TO-15 uses samples collected in evacuated containers, and the sample pressure does not reach atmospheric pressure, to prevent water condensation. The sample pressure is then measured, and the sample container pressurized with inert, dry gas to above atmospheric pressure to allow the sample to flow into the sample concentrator. The sample concentrator uses a water management system to remove water while minimally affecting the target substances, then passes the sample into the concentration step. The water management system takes several minutes to cycle, and that delays the injection of the sample. While this type of system, which is the current state of the art, is successful, the dilution/pressurization step takes time and introduces the possibility of error. Dilution of the sample has a negative effect on system sensitivity. The water management system operation adds several minutes to the time required for each analysis.

Additionally, spacecraft designers are required to recover and remove carbon dioxide from the cabin air, and they need to recover drinking water from all waste streams. The presence of high levels of humidity in the air detracts from the ability of some carbon dioxide removal systems to work at peak efficiency. Additionally, water can be difficult and/or energy expensive to remove from waste while providing sufficient purity for re-use as drinking water.

Additionally, persons working or living, whether in the military or in civilian capacity, in locations with limited availability of potable water have a need to be able to recover potable water from a plurality of sources of nonpotable or toxic or contaminated moisture, including from human waste. Many types of systems for providing potable water are either heavy and require substantial energy input, or have substantial limitations on the types of contamination for which they work properly.

Additionally, water samples collected for analysis often contain trace levels of toxic substances. The analysis of water samples often requires the extraction from the water and subsequent concentration of those trace toxic substances for the analysis to be performed. There is a partition coefficient between the water sample and the extraction medium that sets a lower limit of concentration of the trace toxic substance below which the quantitative nature of the extraction is substantially less than complete, and the accuracy of the analysis is affected detrimentally.

SUMMARY OF THE INVENTION

Graphene oxide membranes have recently been shown to have the property of being essentially transparent to water vapor while being impervious to all other substances, even gases such as helium. In some experiments, a graphene oxide membrane was demonstrated to be virtually transparent to the passage of water vapor while being virtually completely impervious (10,000,000,000 times less throughput) to even permanent gases such as helium. In one example, a bottle of a mixture of ethanol and water was capped with the graphene oxide membrane and, while no ethanol could be detected in the air above the membrane, water evaporated freely, escaping the bottle.

Accordingly, graphene oxide membranes may provide what appears to be a relatively easy solution to water management/recovery issues in analytical chemistry, in spacecraft support systems, and in military and civilian potable water recovery/purification systems. Graphene oxide films, produced from micron-sized flakes of graphene oxide, have the very interesting and useful property of being virtually completely porous to water, but virtually impervious to everything else, even helium. In these applications, it may be desirable to protect the graphene oxide membrane from direct contact with liquid water since such contact may affect the integrity of the film. There are a plurality of ways this can be accomplished without affecting the transport of water vapor through the film. For example, the graphene oxide membrane may be disposed between layers of expanded polytetrafluoroethylene (ePTFE) which allows the passage of water vapor but keeps liquid water from contacting the graphene oxide membrane.

Accordingly, disclosed herein are utilities (e.g., apparatuses and systems) for removing water vapor from a gas stream (e.g., dehumidification, etc.) and for providing water purification, recovery and/or sample concentration. The disclosed utilities employ a graphene oxide or a perforated graphene monolayer membrane to separate liquid water molecules and/or water vapor molecules from gasses, liquids, and other substances such as wet muck (e.g., mixed liquids and solids such as mud or animal waste) as well as aqueous samples prior to testing of the samples. In one embodiment, the perforated graphene monolayer may comprise Perforene™ developed by Lockheed Martin Corporation of Bethesda, Md. Perforene™ has the property of allowing the passage of pure liquid water through the film when sufficient pressure is applied to the contaminated water side of the film. Perforene™ is not affected by contact with liquid water. The graphene oxide membrane may be employed in a device to remove water vapor from a gas stream in a variety of applications that may require dehumidified gas (e.g., gas chromatograph/mass spectrometer gas sample analysis, cabin air purification systems, and water purification and recovery systems, etc.), and the Perforene™ film may be used to remove excess water from contaminated water samples to simplify analysis of contaminants in the water and to provide for improved detection limits. By associating the graphene oxide or perforated graphene monolayer membrane with one or more other elements (e.g., a plurality of lumens, a mixing auger, a thermoelectric device, a movable piston, etc.), the utilities may facilitate the removal of purified water and water vapors from a gas steam or various liquid/solid mixtures while leaving the more concentrated contaminants behind.

A graphene oxide dryer may be provided by a graphene oxide film sandwiched between fine mesh, inert screens and passing the sample gas through the center while surrounding the tube with dry gas. Such a graphene oxide dryer may provide a solution to the water issue facing all trace GC/MS analytical systems. It is anticipated that the target substances will not penetrate the graphene oxide, as was the case for Nafion®. In this regard, the graphene oxide film may be heated sufficiently to prevent the target substances from sticking to the film, and allow them to pass by the film and into the sample concentrator for subsequent injection into the analytical column. If, and only if, target substances stick to the graphene oxide film at moderate temperatures and release completely at higher temperatures, the graphene oxide film may be incorporated into the portion of the system that traps the target substances, otherwise it functions as a dryer only. Additionally, if the graphene oxide dryer is operated in the field at a temperature that will allow water vapor to pass through while not adsorbing any of the target substances, the graphene oxide dryer may be incorporated into the sampling system prior to the evacuated canister and after an inert pressurizing pump, thereby allowing the sample to be pressurized to some degree in the sample canister, thereby eliminating the pressure measurement and pressurization steps currently in use prior to injection into the analytical system. This would improve sensitivity and reduce the chance for analytical error due to incorrect recording of either the initial pressure, or the final pressure, or both.

Regarding analytical chemistry applications, the graphene oxide film dryer has the simplicity of the previous Nafion® dryer without its disadvantages. Unlike Nafion®, graphene oxide films pass only water. This allows simpler sample handling and faster sample processing, and probably even less chance for sample handling artifacts.

Regarding spacecraft systems, it appears that the current systems use much more energy and are more complex than the proposed graphene oxide film dryer. Simple systems are generally more reliable, because there is less that can go wrong. The graphene oxide dryer would require less energy to operate than current technology, and it would simplify the recovery of drinking water from waste. Additionally, manned spacecraft operations require the removal of carbon dioxide from the cabin air, and the humidity of the cabin air requires the use of substantially more carbon dioxide sorbent than would be required if the cabin air were dry. The proposed graphene oxide film dryer would also allow the removal of water vapor from cabin air prior to it being processed by the carbon dioxide removal system, thereby reducing the amount of carbon dioxide sorbent required for a specified length of mission. The water removed from the cabin air would be recycled into the potable water system. This same application would also be useful for submarine air purification systems.

Regarding the use of graphene oxide film dryers for the production of potable water for personnel in hostile environments, various devices of differing water processing capacities can be provided that will allow individuals or groups of individuals to place contaminated, moisture-containing material, including, but not limited to human waste, mud, biologically contaminated material, and chemically contaminated material (including acidic or caustic material) into one compartment of the device, and have potable water be collected in the compartment on the other side of the incorporated graphene oxide film. The graphene oxide dryer is anticipated to require less energy for operation, and can be made sufficiently compact for personal use.

In one aspect, an apparatus for removing water from a gas or liquid may include a first lumen, a second lumen, and a graphene oxide membrane separating the first lumen from the second lumen. The first and second lumens may, for example, be provided by a tubular arrangement including an outer tube and an inner tube, where the inner tube comprises the graphene oxide membrane, and where the inner lumen is provided within an interior surface of the inner tube and the outer lumen is provided between an exterior surface of the inner tube and an interior surface of the outer tube. Water molecules within a humid gas or liquid stream introduced into the first lumen pass through the graphene oxide membrane into a dry gas stream introduced into the second lumen.

In another aspect, a water purification and recovery system may include a container including a first chamber and a second chamber, a heating device operable to heat the first chamber, and a graphene oxide membrane disposed at an interface between the first chamber and the second chamber. A wet muck introduced into the first chamber is heated by heat from the heating device to cause vaporization of at least some portion of the wet muck, and water vapor evaporated from the muck passes through the graphene oxide membrane into the second chamber where the water vapor is cooled and condenses. Condensation of the water vapor may be assisted by operation of a cooling device that cools the second chamber. In this regard, the heating device and the cooling device may together comprise a thermoelectric device disposed in the container and having a heating surface facing the first chamber and a cooling surface facing the second chamber. One or more layers of ePTFE membrane may be provided on either or both sides of the graphene oxide membrane to protect the graphene oxide membrane from liquid water.

In a further aspect, a water purification and recovery system may include a container including a first chamber and a second chamber, a perforated graphene monolayer disposed at an interface between the first chamber and the second chamber, and a piston disposed within the container operable to move the perforated graphene monolayer relative to the first chamber (e.g. to decrease the volume of the first chamber). A wet muck introduced into the first chamber is pressurized (e.g., by operating the piston) and liquid water molecules within the wet muck pass through the perforated graphene monolayer into the second chamber. In this regard, the perforated graphene monolayer may, for example, comprise Perforene™, allowing the passage of liquid water molecules and blocking passage of other molecules and ions.

A water purification and recovery system in which wet muck introduced into the first chamber may be pressurized in order to remove liquid water may be particularly suited to preparing mixed liquid and solid (e.g. wet muck) samples for subsequent analysis. In this regard, by removing water from the wet muck sample such a system reduces the volume of water in the sample thereby increasing the concentration of target analytes to improve analytical results/sensitivity.

Various refinements exist of the features noted in relation to the various aspects of the present disclosure. Further features may also be incorporated in the various aspects of the present disclosure. These refinements and additional features may exist individually or in any combination, and various features of the various aspects may be combined. These and other aspects and advantages of the present disclosure will be apparent upon review of the following Detailed Description when taken in conjunction with the accompanying figures.

DETAILED DESCRIPTION

Figure 1:
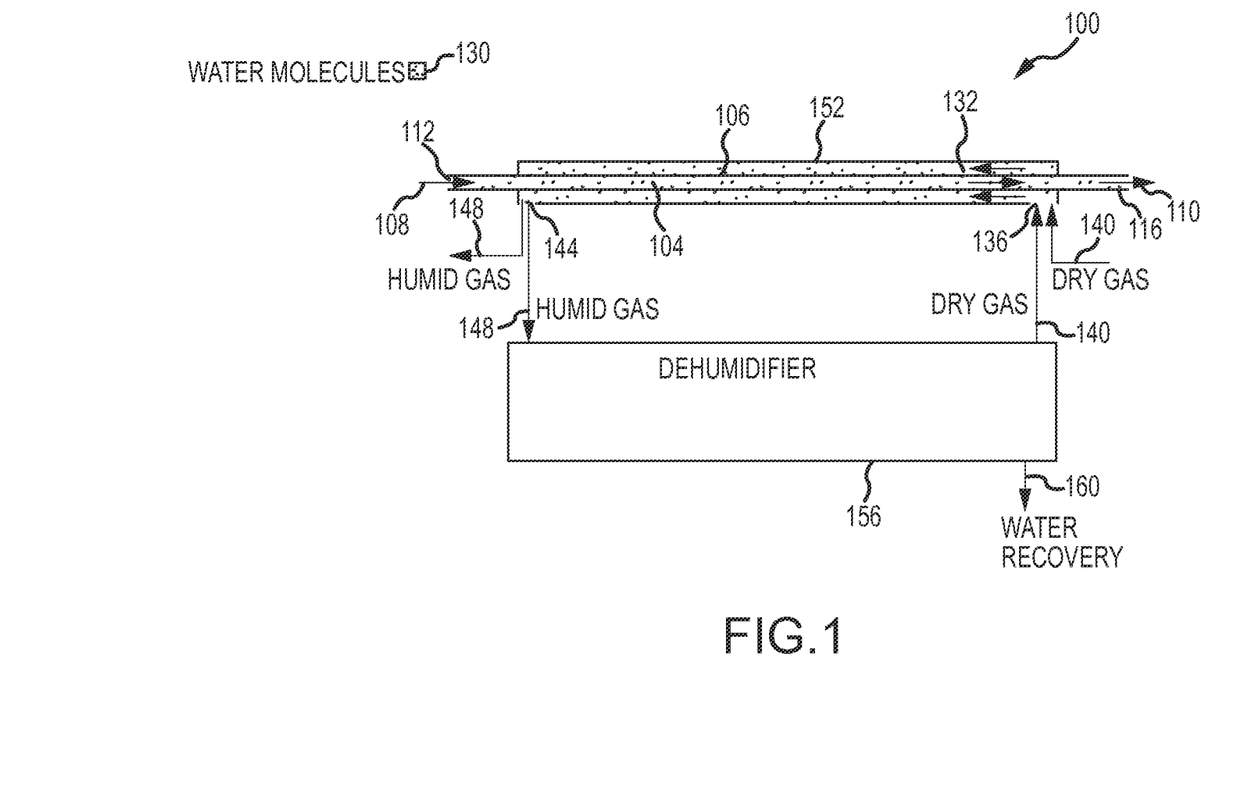
FIG. 1 shows a side view of one embodiment of a graphene oxide dryer or water recovery unit.
Figure 2:
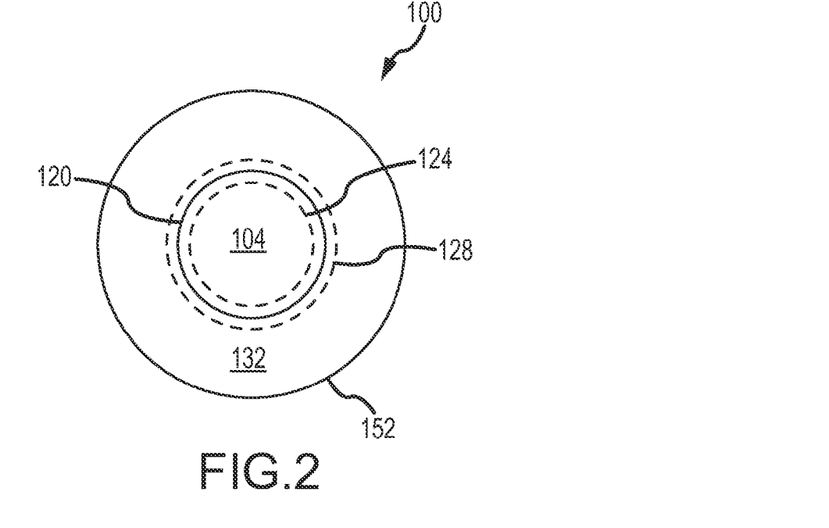
FIG. 2 shows a cross-sectional view of the graphene oxide dryer or water recovery unit of FIG. 1.

Referring to FIGS. 1 and 2, side and cross-sectional views are presented of one embodiment of a graphene oxide dryer unit 100 useful in removing water vapor from a humid gas. The graphene oxide dryer 100 may also function as a water recovery unit for recovering water from a humid gas and/or from a liquid. Broadly, the graphene oxide dryer 100 may include any appropriate structure providing at least two lumens (e.g., a double-walled pipe, a tube within a shell, a tube with a longitudinal separation plate, etc.). In the present embodiment, the graphene oxide dryer 100 may include a first lumen 104 that may receive a humid gas stream 108 at first opening 112 of the first lumen 104 and expel dehumidified gas 110 at a second opening 116 of the first lumen 104.

The first lumen 104 may be provided within the interior of an inner tube 106. The inner tube 106 may include one or more concentric layers that extend for all or a portion of the length of first lumen 104, one layer of which may be a graphene oxide membrane layer 120. The graphene oxide membrane layer 120 may be comprised of a plurality of micron-sized graphene oxide flakes interconnectedly disposed to form a film permeable only by pure, distilled water vapor. Inner tube 106 may also include one or more fine-mesh screen layers that may provide structural support to the graphene oxide membrane 120. In one embodiment, graphene oxide membrane 120 may be positioned concentrically on the outside of an inner fine-mesh screen 124 and concentrically on the inside of an outer fine-mesh screen 128. Graphene oxide membrane 120 may conform to the shape and be supported by the inner fine-mesh screen 124. The outer fine-mesh screen 128 may secure graphene oxide membrane 120 to the inner fine-mesh screen 124 and provide additional structural support to graphene oxide membrane 120. In this regard, inner fine-mesh screen 124 and outer fine-mesh screen 128 may contact each other, for example, at various structural support points located circumferentially on the inner tube 106. Inner fine-mesh screen 124 and outer fine-mesh screen 128 may be substantially porous such that neither inner fine-mesh screen 124 nor outer fine-mesh screen 128 impedes the flow of water molecules into and away from graphene oxide membrane 120. In some embodiments inner fine-mesh screen 124 may possess a different porosity and outer fine-mesh screen 128, and in other embodiments they may have a similar porosity. In other embodiments that may primarily be suited for recovering water from a liquid stream introduced into the first lumen 104, it may be possible for the inner tube 106 to comprise a perforated graphene monolayer (e.g., Perforene™) coupled with an outer reinforcing layer of metal honeycomb material. In this regard, the liquid stream may need to be under high pressure in order force liquid water through the perforated graphene monolayer.

A stream of humid gas (e.g. a gas sample that is to be analyzed or cabin air) may be introduced into the first lumen 104 at the first opening 112 thereof. As the humid gas 108 traverses the length of first lumen 104 from first opening 112 of the first lumen 104 to the second opening 116 of the first lumen 104, water molecules 130 (e.g., water vapors) pass through inner fine-mesh screen 124, graphene oxide membrane 120 and outer fine-mesh screen 128 such that dehumidified gas 110 exits first lumen 104 at the second opening 116 thereof. Other gas molecules and substances (e.g. carbon dioxide, volatile organic and inorganic chemicals) do not pass through the graphene oxide membrane 120 and remain in the dehumidified gas 110. Upon exiting the first lumen 104, dehumidified gas 110 may be directed to various other apparatuses and uses including, for example, to a gas chromatograph/mass spectrometer pre-concentrator for subsequent analysis.

The graphene oxide dryer 100 may also include a second lumen 132. In this regard, the second lumen 132 may be provided between an exterior surface of the inner tube 106 and an interior surface of an outer tube 152 concentrically surrounding and spaced away from the inner tube 106. Second lumen 132 may include a first opening 136 thereof and a second opening 144 thereof. A dry gas 140 from, for example, a compressed gas cylinder (not shown), may be introduced into the second lumen 132 through the first opening 136 thereof. As dry gas 140 traverses the length of second lumen 132 from the first opening 136 of the second lumen 132 to the second opening 144 of the second lumen 132, it receives water molecules 130 that pass through the graphene oxide membrane 120 resulting in a humidified gas 148 that exits second lumen 132 at second opening 144 thereof. In other embodiments, the position of first lumen 104 with respect to second lumen 132 may be changed. For example, the second lumen could be provided on the interior of the inner tube, and the first lumen could be provided between the exterior surface of the inner tube and the interior surface of the outer tube.

In some applications (e.g., in recovering water from cabin air or from an animal waste such as from human excrement and/or urine) the graphene oxide dryer 100 may be coupled with a dehumidification module 156. In this regarding, the humid gas 148 exiting the second lumen 132 may be directed to a dehumidification module 156 that removes water from the humid gas 148 and directs the water to a water recovery module 160. In this regard the dehumidification module 156 may output a dehumidified or dry gas 140 that may be reintroduced into the second lumen 132 in lieu of or in addition to dry gas 140 from a compressed gas cylinder (not shown).

Figure 3:
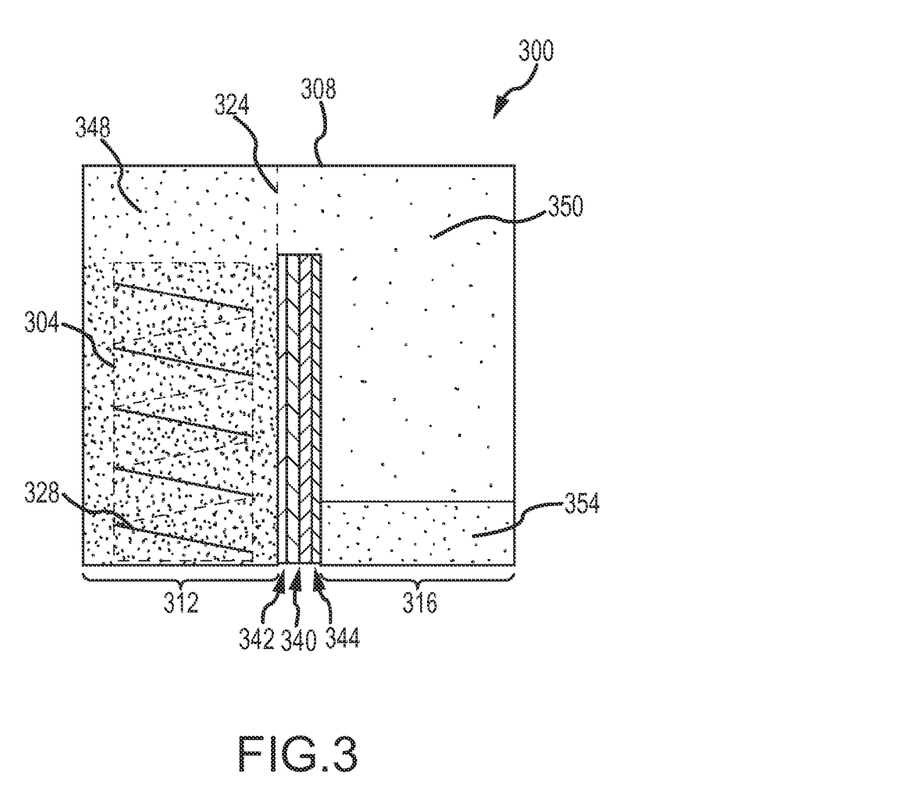
FIG. 3 shows a side cross-sectional view of one embodiment of a simplified graphene oxide water purification or recovery system.

FIG. 3 presents a side cross-sectional view of one embodiment of a simplified graphene oxide water purification or recovery system 300 that may be used to recover purified water from wet muck 304 or the like. Wet muck 304 may, for example, include liquid and/or moisture-containing solid components that may be chemically or biologically contaminated (e.g., mud, excrement and/or urine from humans and/or other animals, etc.). Graphene oxide water purification system 300 may include a container 308 including a first chamber 312 and a second chamber 316. The first chamber 312 may be separated from the second chamber 316 by a thermoelectric device 340 and a graphene oxide membrane 324, all disposed within the container 308. The thermoelectric device 340 may include a heating side surface side 342 oriented nearest the first chamber 312 and a cooling side surface 344 oriented nearest the second chamber 316. The thermoelectric device 340 may be disposed on and extend up from a bottom surface of the container 308, thereby creating an impervious barrier between the first chamber 312 and the second chamber 316. Graphene oxide membrane 324 may be disposed on and extend down from a top surface of the container 308 such that it extends to, and is fixedly interconnected with, a top edge of the thermoelectric device 340. In this regard, a water molecule permeable interface between first chamber 312 and second chamber 316 may be provided by the graphene oxide membrane 324 through which water molecules may pass while other substances are substantially blocked.

In one embodiment, the wet muck 304 may be introduced into the first chamber 312. In this regard, the container 308 may, for example, have a removable lid (not shown). A mixing auger 328 may be disposed within first chamber 312. The wet muck 304 may be mixed by mixing auger 328 to facilitate homogenization of the wet muck 304 inside the first chamber 312 and consistent distribution of the wet muck 304 over the heating side surface 342 of the thermoelectric device 340. In this regard, the thermoelectric device 340 may be operated to cause the heating side surface 342 to heat the first chamber 312, which, consequently, may increase the temperature of the wet muck 304 therein to the point that mixed vapors 348 including water molecules rise through and from the wet muck 304 and congregate at the top of the first chamber 312.

As mixed vapors 348 are generated within first chamber 312, the mixed vapors 348 contact the graphene oxide membrane 324. In this regard, as mixed vapors 348 contact graphene oxide membrane 324, only pure, water vapor molecules 350 may pass through the graphene oxide membrane 324 and subsequently into the second chamber 316. In this regard, as wet muck 304 is heated and agitated, water vapors 350 begin to collect in second chamber 316. Likewise, when the thermoelectric device 340 is operated, the cooling side surface 344 cools the second chamber 316 which, consequently, may cool the water vapor molecules 350 within the second chamber causing the water molecules to condense and collect as liquid water 354 at the bottom of the second chamber 316.

Figure 4:
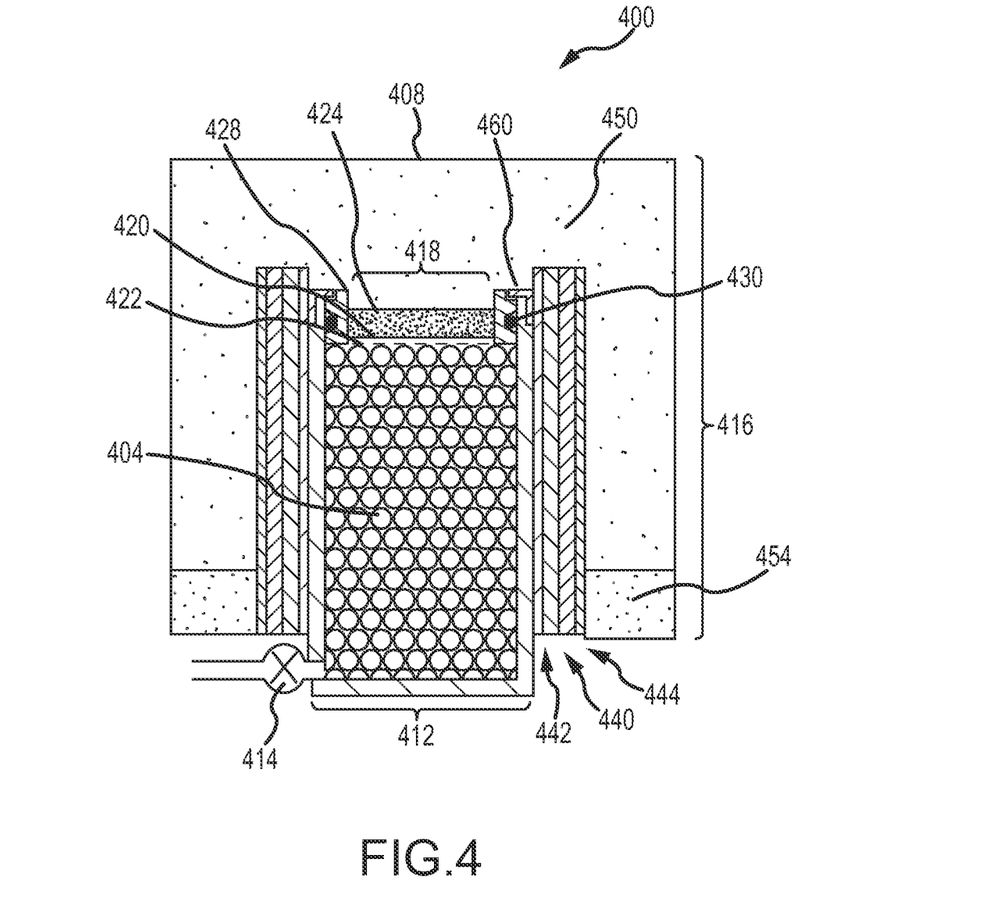
FIG. 4 shows a side cross-sectional view of another embodiment of a simplified graphene oxide water purification or recovery system.

FIG. 4 presents a side cross-sectional view of another embodiment of a simplified graphene oxide water purification or recovery system 400 that may be used to remove water from wet muck 404 and/or aqueous samples by removing water from wet muck 404 or the like. The graphene oxide water purification or recovery system 400 may include a container 408 having a first chamber 412 and a second chamber 416. A thermoelectric device 440 may be disposed on and extend upward from a bottom inner surface of the container 408 to provide an impermeable boundary between the first chamber 412 and the second chamber 416. The thermoelectric device 440 may include a heating side surface side 442 oriented nearest the first chamber 412 and a cooling side surface 444 oriented nearest the second chamber 416.

A water molecule permeable interface between the first chamber 412 and the second chamber 416 may be provided by a filter membrane structure 418. The filter membrane structure 418 may be fixedly attached to a piston 428. The piston 428 may be slidably engaged with an interior surface of the first chamber 412 such that the piston 428 and also the filter membrane structure 418 fixedly attached thereto may slide relative to the interior of the first chamber 412. Accordingly, the internal volume of the first chamber 412 may vary based on the position of piston 428. A seal element 430 (e.g. a suitable elastomer o-ring) may be provided between a side of the piston 428 and the interior surface of the first chamber 412 in order to mitigate the possibility of wet muck 404 leaking from the first chamber 412 into the second chamber 416.

The filter membrane structure 418 may include a graphene oxide membrane layer 420, a replaceable ePTFE membrane layer 422, and a metal honeycomb reinforcement layer 424. Graphene oxide membrane layer 420 may be comprised of a plurality of micron-size graphene oxide flakes interconnectedly disposed to form a film permeable only by pure, distilled water. In one embodiment, graphene oxide membrane layer 420 may be positioned laterally above the ePTFE membrane layer 422 and laterally below metal honeycomb reinforcement layer 424. As such, the replaceable ePTFE membrane layer 422 may provide an interface between wet muck 404 and graphene oxide membrane layer 420 such that the replaceable ePTFE membrane layer 422 may preclude direct contact of graphene oxide membrane layer 420 with wet muck 404. Metal honeycomb reinforcement layer 424 may provide structural support to graphene oxide membrane layer 420. Replaceable ePTFE layer 422 and honeycomb reinforcement layer 424 may be substantially porous such that neither ePTFE membrane layer 422 nor honeycomb reinforcement layer 424 impedes water vapor flow into and through graphene oxide membrane layer 420. In other embodiments, filter membrane structure 418 may comprise a perforated graphene monolayer (e.g., Perforene™) coupled with the reinforcing layer of metal honeycomb material 424 and the ePTFE membrane 422.

Wet muck 404 may be introduced into the first chamber 412 at inlet port 414 that may be opened and closed as necessary. In this regard, a pump (not shown) may be used to pump the wet muck 404 into the first chamber 412 As wet muck 404 fills the first chamber 412, piston 428 moves laterally upwards until piston 428 reaches the top most portion of the first chamber 412 where its upward movement is stopped by a stop ring protrusion 460. The thermoelectric device 440 may be operated so that the heat side surface 442 heats the first chamber 412 and in turn the wet muck 404 introduced therein. As the temperature of the wet muck 404 increases, water molecules and other substances may be vaporized within the wet muck 404. Further, the pump (not shown) may be operated in an effort to introduce additional wet muck 404 into the full first chamber 412 thereby pressurizing the first chamber 412 relative to the second chamber 416. The pressure differential between the first chamber 412 and the second chamber 416 may additionally encourage vaporized water molecules 450 to pass through the graphene oxide membrane 420 included within filter membrane structure 418 while other substances are blocked by the graphene oxide membrane 420. In this regard, the pump may need to be calibrated in order to measure the total volume of wet muck 404 introduced into the first chamber 412 as subsequent analysis may depend on the original volume (unconcentrated volume) being known accurately. In this regard, either the volume of the first chamber 412 is known, and once filled it is not refilled, or the pump delivers the sample in such a manner as to keep track of the total volume introduced into the first chamber 412.

The vaporized water molecules 450 passing through the filter membrane structure 418 enter the second chamber 416. When the thermoelectric device 440 is operated to heat the wet muck 404, the cooling side surface 444 likewise cools the second chamber 416 which, consequently, may cool the water vapor molecules 450 within the second chamber 416 causing the water molecules 450 to condense and collect as liquid water 454 at the bottom of the second chamber 416. In other embodiments, it may be possible to heat the first chamber 412 while cooling the second chamber 416 without the need for a thermoelectric device 440 or other heating/cooling devices. For example, one could use other heating and cooling sources such as, for example, coals from a camp fire while the other side is placed in a cool stream.

After some portion of the water has been removed from the wet muck 404, the wet muck 404 may be removed by pulling it through the port 414 by, for example, reversing the pump. In some embodiments, it may also be possible to disengage the first chamber 412 from the second chamber 416, and to manually push the piston 418 to its original position (e.g. at or near the bottom of the first chamber 412), forcing the aqueous sample/muck 404 out of the device and into a concentrated sample receiver (not shown).

A system 400 such as depicted in FIG. 4 may be used to remove water from an aqueous sample collected in the first chamber 412, with the piston 428 maintaining contact with the aqueous sample to prevent loss of volatile target contaminants from the aqueous sample which will be subsequently analyzed. In this regard, since volatiles are normally part of an analysis, it is desirable to prevent the formation of free headspace into which the volatile substances may escape from the aqueous sample. The volume of the aqueous sample will be determined by the volume with the piston at the stop on the top of the system, so even with the water removed, once the remaining partially dewatered sample is removed for analysis, the volume of the sample will be taken to be equal to the volume of the first chamber with the piston at the top. The lack of headspace formation ensures that all volatiles remain in the aqueous portion. If someone were to remove too much of the water, the solubility of some of the target substances might be exceeded, and the volatile substances could escape as a gas possibly harming the integrity of the sample. This scenario would only be possible if there were very high concentrations of the volatile substance dissolved in the water, in which case, it is likely a GC/MS concentrator would not be used because the concentrations of the target substances would exceed the normal analytical range of the GC/MS.

Figure 5:
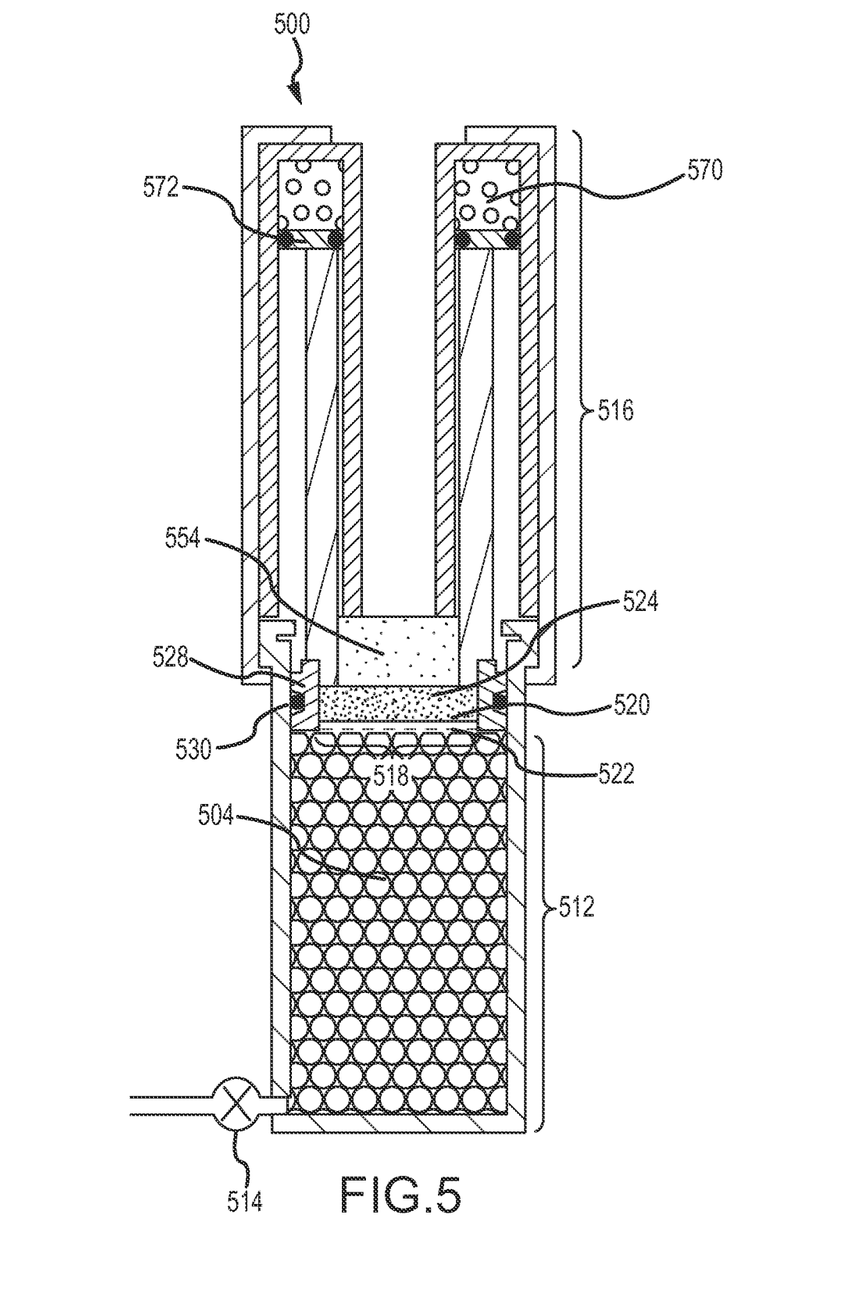
FIG. 5 shows a side cross-sectional view of one embodiment of a simplified perforated graphene monolayer water purification or recovery system.

FIG. 5 presents a side cross-sectional view of another embodiment of a simplified perforated graphene monolayer water purification or recovery system 500 that may be used to remove water from aqueous samples and/or wet muck 504 by recovering water from wet muck 504 or the like. The perforated graphene monolayer water purification or recovery system 500 may include a container 508 having a first chamber 512 and a second chamber 516.

A water molecule permeable interface between the first chamber 512 and the second chamber 516 may be provided by a filter membrane structure 518. The filter membrane structure 518 may be fixedly attached to a piston 528. The piston 528 may be slidably engaged with an interior surface of the first chamber 512 such that the piston 528 and also the filter membrane structure 518 fixedly attached thereto may slide relative to the interior of the first chamber 512. Accordingly, the internal volume of the first chamber 512 may vary based on the position of piston 528. A seal element 530 (e.g. a suitable elastomer o-ring) may be provided between a side of the piston 528 and the interior surface of the first chamber 512 in order to mitigate the possibility of wet muck 504 leaking from the first chamber 412 into the second chamber 516. The piston 528 may be operated by application of pressurized hydraulic fluid 570 against a piston head 572 that generates force to push the piston 528 and filter membrane structure 518 downwardly against the wet muck 504.

The filter membrane structure 518 may include a perforated graphene monolayer (e.g., Perforene™) 520, a replaceable ePTFE membrane layer 522, and a metal honeycomb reinforcement layer 524. In one embodiment, the perforated graphene monolayer layer 520 may be positioned laterally above the ePTFE membrane layer 522 and laterally below metal honeycomb reinforcement layer 524. As such, the replaceable ePTFE membrane layer 522 may provide an interface between wet muck 504 and perforated graphene monolayer 520 such that the replaceable ePTFE membrane layer 522 may preclude direct contact of perforated graphene monolayer 520 with wet muck 504. Metal honeycomb reinforcement layer 524 may provide structural support to perforated graphene monolayer 520. Replaceable ePTFE layer 522 and honeycomb reinforcement layer 524 may be substantially porous such that neither ePTFE membrane layer 522 nor honeycomb reinforcement layer 524 impedes liquid water molecule flow into and through perforated graphene monolayer 520. In other embodiments, filter membrane structure 518 may comprise a graphene oxide layer coupled with the reinforcing layer of metal honeycomb material 524 and the ePTFE membrane 522.

Wet muck 504 may be introduced into the first chamber 512 at inlet port 514 that may be opened and closed as necessary. In this regard, a pump (not shown) may be used to pump the wet muck 504 into the first chamber 512. The piston 528 may be operated to press against the wet muck 504 in the first chamber thereby forcing liquid water molecules 554 in the wet muck to pass through the filter membrane structure 518 and enter the second chamber 516 where the water 554 is collected. In this regard, piston 528 may be operated by application of hydraulic pressure via a compressed liquid or gas. Additionally, in some embodiments, a perforated graphene monolayer water purification or recovery system 500 such as depicted in FIG. 5 may also include an optional replaceable pre-filter (not shown) positioned (e.g., at the inlet to the first chamber 504 from the pump 514 or removably attached to the face of the piston 528 facing the first chamber 512 between the contents of the first chamber 512 and the filter membrane structure 518) to minimize possible plugging of the filter membrane structure 518 with some sample matrices.

After some portion of the water has been removed from the wet muck 504, the wet muck 504 may be removed by pulling it through the port 414 by, for example, reversing the pump. In some embodiments, it may also be possible to disengage the first chamber 512 from the second chamber 516, and to manually push the piston 518 to its original position (e.g. at or near the bottom of the first chamber 512), forcing the aqueous sample/muck 504 out of the device and into a concentrated sample receiver (not shown).

While this disclosure contains many specifics, these should not be construed as limitations on the scope of the disclosure or of what may be claimed, but rather as descriptions of features specific to particular embodiments of the disclosure. Certain features that are described in this specification in the context of separate embodiments and/or arrangements can also be implemented in combination in a single embodiment. Conversely, various features that are described in the context of a single embodiment can also be implemented in multiple embodiments separately to in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Additionally, the foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiment to the extent permitted by the prior art.

What is claimed is:

1. A water purification and recovery system comprising:
   a container including a first chamber and a second chamber;
   a heating device that heats the first chamber;
   a graphene oxide membrane disposed at an interface between the first chamber and the second chamber, wherein a wet muck or aqueous sample introduced into the first chamber is heated by heat from the heating device to cause vaporization of at least some portion of the wet muck or aqueous sample, and wherein water molecules within the vaporized muck or aqueous sample pass through said graphene oxide membrane into the second chamber; and
   a cooling device that cools the second chamber, wherein the second chamber is cooled by the cooling device to the point that water molecules passing through said graphene oxide membrane into the second chamber condense within the second chamber and collect as liquid water in the second chamber,
   wherein said heating device and said cooling device together comprise a thermoelectric device having a heating surface and a cooling surface, and wherein said thermoelectric device is disposed within said container and oriented to have the heating surface thereof facing the first chamber and the cooling surface thereof facing the second chamber.

2. The system of claim 1, wherein said thermoelectric device separates the first chamber from the second chamber.

3. The system of claim 1, further comprising:
   a mixing auger operable to mix the wet muck or aqueous sample introduced into the first chamber.

4. The system of claim 1, further comprising:
   a pump operable to introduce the wet muck or aqueous sample into the first chamber.

5. The system of claim 1, further comprising:
   a removable expanded polytetrafluoroethylene (ePTFE) membrane disposed between said graphene oxide membrane and the first chamber.

6. The system of claim 1, further comprising:
   a metal honeycomb reinforcing layer disposed between said graphene oxide membrane and the second chamber.

7. A water purification and recovery system, comprising:
   a container including a first chamber and a second chamber;
   a thermoelectric device having a heating surface and a cooling surface, wherein said thermoelectric device is disposed within said container and orientated to have the heating surface thereof facing the first chamber and the cooling surface thereof facing the second chamber;
   a perforated graphene monolayer disposed at an interface between the first chamber and the second chamber; and
   a piston disposed within the container operable to move said perforated graphene monolayer relative to the first chamber, wherein a wet muck or aqueous sample introduced into the first chamber is pressurized by operating said piston, and wherein liquid water molecules within the wet muck pass through said perforated graphene monolayer into the second chamber.

8. The system of claim 7, further comprising:
   a pump operable to introduce the wet muck or aqueous sample into the first chamber.

9. The system of claim 7, further comprising:
   a removable expanded polytetrafluoroethylene (ePTFE) membrane disposed between said perforated graphene monolayer and the first chamber.

10. The system of claim 7, further comprising:
    a metal honeycomb reinforcing layer disposed between said perforated graphene monolayer and the second chamber.

11. The system of claim 7, wherein said piston is mechanically operated.

12. The system of claim 7, wherein said piston is hydraulically operated.

13. The system of claim 7, wherein the heating surface heats the first chamber.

14. The system of claim 7, wherein the cooling surface cools the second chamber to the point that water molecules passing through said graphene oxide membrane into the second chamber condense within the second chamber and collect as liquid water in the second chamber.

* * * * *